(12) United States Patent
Endo et al.

(10) Patent No.: US 8,231,522 B2
(45) Date of Patent: Jul. 31, 2012

(54) ELECTRONIC ENDOSCOPE SYSTEM

(75) Inventors: Azuchi Endo, Saitama (JP); Masaki Takamatsu, Saitama (JP); Yasufumi Takahashi, Kanagawa (JP); Kazuhiro Nishida, Miyagi (JP); Takashi Kido, Miyagi (JP); Hiroyuki Hasegawa, Saitama (JP); Yasunori Ohta, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 203 days.

(21) Appl. No.: 12/561,050

(22) Filed: Sep. 16, 2009

(65) Prior Publication Data

US 2010/0069713 A1   Mar. 18, 2010

(30) Foreign Application Priority Data

Sep. 18, 2008 (JP) .................................. 2008-239328

(51) Int. Cl.
*A61B 1/04* (2006.01)
*A61B 1/06* (2006.01)
(52) U.S. Cl. ................ 600/109; 600/160; 600/178
(58) Field of Classification Search .................. 600/118, 600/181, 109, 160, 178, 182, 476–478; 250/458.1, 250/484.2, 461.2
See application file for complete search history.

(56) References Cited

U.S. PATENT DOCUMENTS

| | | | | |
|---|---|---|---|---|
| 4,942,473 A * | 7/1990 | Zeevi et al. | | 348/281 |
| 5,909,247 A * | 6/1999 | Hosokai et al. | | 348/302 |
| 6,124,888 A * | 9/2000 | Terada et al. | | 348/302 |
| 6,130,420 A * | 10/2000 | Tanaka et al. | | 250/208.1 |
| 6,498,948 B1 * | 12/2002 | Ozawa et al. | | 600/476 |
| 6,570,615 B1 * | 5/2003 | Decker et al. | | 348/272 |
| 6,972,791 B1 * | 12/2005 | Yomeyama | | 348/230.1 |
| 7,209,170 B2 * | 4/2007 | Nishino et al. | | 348/302 |
| 7,393,321 B2 * | 7/2008 | Doguchi et al. | | 600/109 |
| 7,664,174 B2 * | 2/2010 | Avni et al. | | 375/240.01 |
| 7,718,945 B2 * | 5/2010 | Sugiyama et al. | | 250/208.1 |
| 7,745,771 B2 * | 6/2010 | Troxell et al. | | 250/208.1 |
| 2002/0161282 A1 * | 10/2002 | Fulghum | | 600/160 |
| 2003/0176768 A1 | 9/2003 | Gono et al. | | |
| 2006/0149133 A1 | 7/2006 | Sugimoto et al. | | |
| 2006/0198620 A1 | 9/2006 | Watanabe | | |
| 2007/0014553 A1 | 1/2007 | Endo | | |
| 2007/0055099 A1 * | 3/2007 | Kimoto | | 600/109 |
| 2007/0097294 A1 * | 5/2007 | Tsukimura | | 349/110 |

(Continued)

OTHER PUBLICATIONS

United States Office Action dated Apr. 24, 2012, in U.S. Appl. No. 12/556,496.

(Continued)

*Primary Examiner* — Philip R Smith
*Assistant Examiner* — William Chou
(74) *Attorney, Agent, or Firm* — McGinn IP Law Group, PLLC

(57) ABSTRACT

An electronic endoscope system includes an electronic endoscope having a CMOS image sensor on the tip of an insertion section, a light source device for illuminating the interior of a patient's body, and a processing device for reading out image signals from the CMOS image sensor. The electronic endoscope system can operate with a standard imaging mode and a special imaging mode. When the time taken to read out the image signals from all the pixels in the standard mode is defined as T, the light source device in the special imaging mode emits illumination light in every first half period T/2 while switching a wavelength of the illumination light between two different wavebands. In every second half period T/2, the processing device reads out the image signals from the half of the pixels.

13 Claims, 6 Drawing Sheets

U.S. PATENT DOCUMENTS

| | | | |
|---|---|---|---|
| 2008/0018733 A1 | 1/2008 | Hasegawa | |
| 2008/0027278 A1* | 1/2008 | Mizuno | 600/109 |
| 2008/0043469 A1 | 2/2008 | Watanabe et al. | |
| 2008/0158380 A1* | 7/2008 | Mabuchi | 348/222.1 |
| 2008/0239070 A1* | 10/2008 | Westwick et al. | 348/68 |
| 2009/0316030 A1* | 12/2009 | Dai | 348/300 |

OTHER PUBLICATIONS

United States Office Action dated May 2, 2012, in U.S. Appl. No. 12/556,481.

* cited by examiner

ELECTRONIC ENDOSCOPE SYSTEM

FIELD OF THE INVENTION

The present invention relates generally to electronic endoscope systems, and more particularly to an electronic endoscope system for visualizing the interior of a patient's body using a CMOS image sensor while changing the waveband of illumination light.

BACKGROUND OF THE INVENTION

In the field of medicine, electronic endoscope systems are widely used. In a diagnostic procedure using the electronic endoscope system, an electronic endoscope is inserted into a body cavity of a patient to capture an image of an internal body part using a miniature image sensor provided at a tip of a slender insertion section. Some of the recent endoscope systems have an ability to switch the wavelength of illumination light for lighting the internal body part between several wavebands (see, United State Patent Application Publications No. 2008/0043469 A1 and No. 2006/0198620 A1). To the body tissue or structure difficult to observe under white visible light (hereinafter, normal light), for example, the light of a specific wavelength other than the normal light (hereinafter, special light, regardless of waveband) is emitted. Changing the illumination condition in this manner allows for emphasizing the body tissue, structure or lesion in the captured image.

Generally, the electronic endoscope system includes either a CMOS or CCD image sensor. The CMOS image sensor consumes less power, and fits on a single board along with peripheral circuitries. A typical CMOS image sensor incorporates a so-called rolling shutter technique that performs exposure of pixels and readout of signal charges (image signals) on every horizontal line in a single picture (frame). Therefore, with the rolling shutter technique, exposure timing is different on every horizontal line, and in capturing a moving object, the image is deformed in the moving direction. Moreover, the pixel amplifiers differ in performance, and may cause a particular noise to degrade the image quality.

The CCD image sensor, by contrast, can produce high-sensitivity, high-resolution images although it uses more power and has structure-inherent problems such as smear and blooming. Configured to expose all the pixels at once, the CCD image sensor can ensure the synchronization of the pixels in a single frame, preventing the deformation of a moving image. Since the organs are always moving, the CCD image sensor is often used in the endoscope systems.

Meanwhile, the recent technology improves the CMOS image sensors to achieve the image quality equal to or better than the CCD image sensors. This improvement gives an impetus for incorporating the mass-productive and low power consumption CMOS image sensors in the electronic endoscope systems.

As mentioned above, the CCD image sensors can synchronize all the pixels in a single frame. Accordingly, in capturing two or more successive frames (i.e., movie), changing the wavelength of the illumination light to the frame rate of the CCD image sensor will lead to produce successive images of different illumination conditions.

However, the CMOS sensors use the rolling shutter, which causes one frame difference in exposure timing between the first and last horizontal lines. Accordingly, if the wavelength of illumination light is changed at the frame rate in capturing two or more successive frames, the last horizontal line is exposed after the change of the wavelength. Each frame results to have the horizontal lines exposed under different illumination conditions, it is impossible to obtain the images of different illumination conditions successively.

SUMMARY OF THE INVENTION

In view of the foregoing, it is a main object of the present invention to provide an electronic endoscope system for producing images under different illumination conditions consecutively.

Another object of the present invention is to provide an electronic endoscope system having a simple structure and convenient operation.

In order to achieve the above and other objects, the electronic endoscope system according to the present invention includes a CMOS image sensor, a light source device, a signal reader and a signal processor. The CMOS image sensor has a plurality of pixels in a two dimensional array. This CMOS image sensor captures an image of the region of interest under illumination light, and generates image signals. The light source device turns on and off a light source repeatedly to emit the illumination light. Every time the light source is turned on, the light source device switches a wavelength of the illumination light between at least two wavebands. The signal reader reads out the image signals from all or a part of the pixels while the light source is turned off. The signal processor produces two kinds of endoscopic images based on the image signals read out by the signal reader.

Preferably, the electronic endoscope system further includes a monitor for displaying the two kinds of endoscopic images at once.

In a preferred embodiment of the present invention, when the time taken to read out the image signals from all the pixels is defined as T, the light source device turns on the light source in every first T/2 period, and the signal reader reads out the image signals from half of the pixels in every second T/2 period. In this embodiment, the signal reader uses an interlace scanning method to read out the image signals.

In another preferred embodiment of the present invention, the light source device turns on the light source in every preceding T period, and the signal reader reads out the image signals from all the pixels in every succeeding T period.

Preferably, the light source device and the signal reader are configured to operate on first and second imaging modes. When the time taken to read out the image signals from all the pixels is defined as one frame period, the light source device in the first imaging mode turns on the light source in every first half frame period. Then, the signal reader reads out the image signals from half said pixels in every second half frame period. In the second imaging mode, a frame rate is changed to N/2 when the frame rate of the first imaging mode is defined as N, and the image signals are read out from all the pixels.

It is preferred to provide the electronic endoscope system with a resetting device for releasing signal charges from the pixels after the readout of the imaging signals every time the light source is turned off.

This resetting device is preferably configured to reset the pixels on the same horizontal line. Alternatively, the resetting device is configured to reset all the pixels at once.

According to the present invention, the light source is turned on and off repeatedly, and the illumination light is switched between different wavebands every time the light source is turned on. The image signals are read out from the pixels of the image sensor while the light source is turned off. This process enables for producing successive images of different illumination conditions using the CMOS image sensor.

Turning off the light source during the readout of the image signals results in synchronizing the exposure timing of all the pixels even with the rolling shutter technique. The rolling shutter artifact, or the deformation of image is thereby prevented without using of a mechanical shutter or the like. As a result, the structure of the electronic endoscope is simplified.

By switching between the first and second imaging modes, it is possible to obtain an appropriate image for every diagnostic examination and treatment. In addition, the images two different kinds can be displayed next to each other. Therefore, the electronic endoscope system becomes more convenient than ever.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENTS

Figure 1:
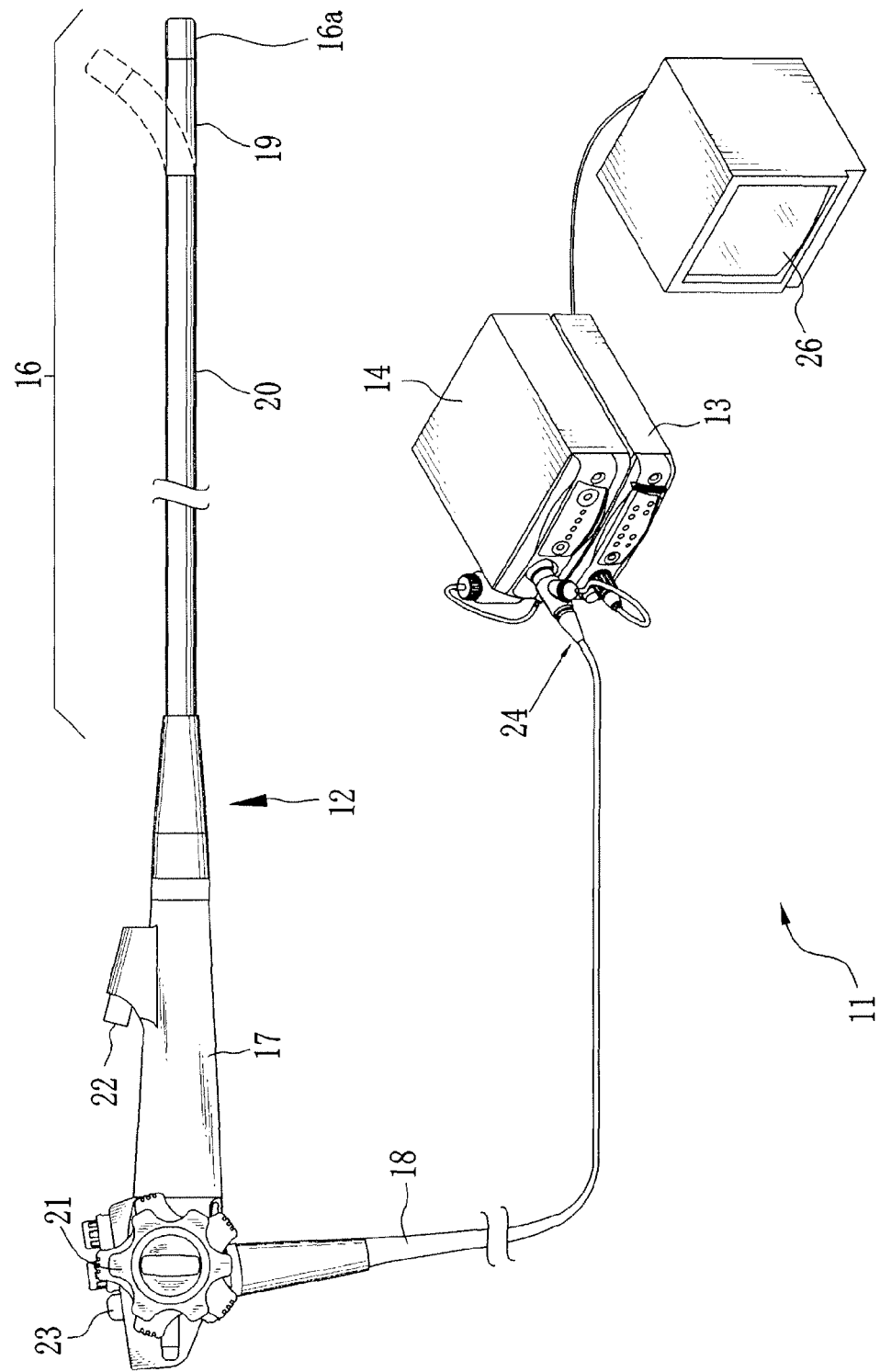
FIG. 1 is an external view of an electronic endoscope system according to the present invention.

Referring to FIG. 1, an electronic endoscope system 11 includes an electronic endoscope (hereinafter, endoscope) 12, a processing device 13 and a light source device 14. The endoscope 12 is composed of an insertion section 16 to be inserted into a patient's body, a handling section 17 connected to a proximal end of the insertion section 16, and a universal cord 18. The insertion section 16 includes a long and slender flexible portion 20, a bending portion 19 and a distal portion 16a, and is able to bend in any directions to assume the shape of a tubular passage in the body.

The bending portion 19 is connected to a rear end of the distal portion 16a. The bending portion 19 is composed of a plurality of annular joint pieces pivotally linked to one another, and coupled to an angle knob 21 on the handling section 17 via a tensioning wire (not shown) running through the insertion section 16. The bending portion 19 bends up, down, right and left as the angle knob is rotated to push and pull the tensioning wire.

Along with the angle knob 21, the handling section 17 is also equipped with a forceps insertion port 22 and several operation buttons including an air/water feed button 23. The forceps insertion port 22 provides an entrance for a medical instrument typically composed of a wire and a syringe needle or a high-frequency knife at the wire tip. The air/water feed button 23 is depressed to spray air or rinse water supplied from an air/water supply device (not shown).

The universal cord 18 connects the endoscope 12 to the processing device 13 electrically, and the endoscope 12 to the light source device 14 optically through a connector 24 at the tip thereof.

The processing device 13, connected also to the light source device 14 and a monitor 26, controls the operation of the electronic endoscope system 11. The light source device 14 emits illumination light toward a light guide 53 (see, FIG. 2) that runs through the universal cord 18 and the insertion section 16.

The endoscope 12 has a timing generator (TG) 42, an A/D converter 45 and a CPU 52, besides a CMOS sensor 31. The CPU 52 communicates with a CPU 61 of the processing device 13, and controls each component of the endoscope 12. In response to a signal from the CPU 61 of the processing device 13, the CPU 52 directs the TG 42 to generate a predetermined timing signal so as to adjust the timing of image signal readout, the reset timing of the CMOS sensor 31 and the conversion timing of the A/D converter 45. The CMOS sensor 31 is reset while the illumination light goes out after the image signal readout. The CPU 52 also enters the amplification adjustment signal into the output circuit 37 so as to obtain appropriately amplified image signals from the CMOS sensor 31.

The processing device 13 includes the CPU 61, a DSP 62, a D/A converter 63 and a RAM 64.

The CPU 61 controls each component of the processing device 13. Communicating with the CPU 52 of the endoscope 12 and a CPU 71 of the light source device 14, the CPU 61 also controls the operation of the endoscope 12 and the light source device 14.

The DSP 62 applies various types of signal processing, such as color interpolation, white balance adjustment and gamma correction, to the image signals out of the CMOS sensor 31. After the signal processing by the DSP 62, the image signals are stored as image data in the RAM 64. The image signals are processed on a frame basis. In the case of switching the illumination light between normal light and special light at a frame rate, the image signals under the normal light and the image signals under the special light are separately processed, and then stored as normal light image data and special light image data in the RAM 64. The DSP 62 also retrieves the image data from the RAM 64, and converts it into an NTSC or similar video signal. This video signal is converted into an analog signal by the D/A converter 63, and displayed on the monitor 26.

The light source device 14 includes the CPU 71, a light source 72 and a wavelength selection filter 73. The CPU 71 communicates with the CPU 61 of the processing device 13, and activates the light source 72 and the wavelength selection filter 73 in synchronization with the operation of the CMOS sensor 31.

The light source 72 is a xenon lamp, a halogen lamp or any similar conventional lamp capable of providing high-intensity light over a broad waveband. Under the control of the CPU 71, the light source 72 emits the illumination light periodically in accordance with exposure and readout timing of the CMOS sensor 31. The illumination light from the light source 72 is efficiently focused onto an entrance of the light guide 53 by a condenser lens 74.

The wavelength selection filter 73 transmits only a specific wavelength component of the illumination light out of the light source 72. Under the control of the CPU 71, the wavelength selection filter 73 is inserted or removed from between the light source 72 and the condenser lens 74 by a driver 73a. The use of the wavelength selection filter 73 provides options of the illumination light, not only white visible light (hereinafter, normal light) but also non-visible light including infrared light and special visible light of a particular RGB ratio.

In the diagnostic examination using the electronic endoscope system 11, the waveband of the illumination light is selected according to the type of the body part (for example, membrane or submucous vessel) and the type of the lesion being observed. The illumination light is preferably switched to a more appropriate waveband during the diagnostic examination with monitoring the endoscopic image. Alternatively, the light source 72 may be composed of two or more LEDs or laser diodes. In this case, each diode is turned on and off separately, instead of using the wavelength selection filter 73, to switch the illumination light between the normal light and the special light.

The electronic endoscope system 11 can work on two different imaging modes; a standard imaging mode using the illumination light of a fixed waveband, and a special imaging mode using two kinds of illumination light in different wavebands for producing endoscopic images under the normal light (hereinafter, normal light image) and under the special light (hereinafter, special light image) alternately.

More particularly, the special imaging mode includes a first special imaging mode (hereinafter, first imaging mode) 81 and a second special imaging mode (hereinafter, second imaging mode) 82 working on a frame rate of N/2 as the frame rate of the first imaging mode 81 is N, and these modes are switchable.

The first imaging mode 81 can complete a series of process, from exposure to image signal readout, within the time taken for the image signal readout in the standard imaging mode, by reducing the number of pixels for each endoscopic image.

Figure 3:
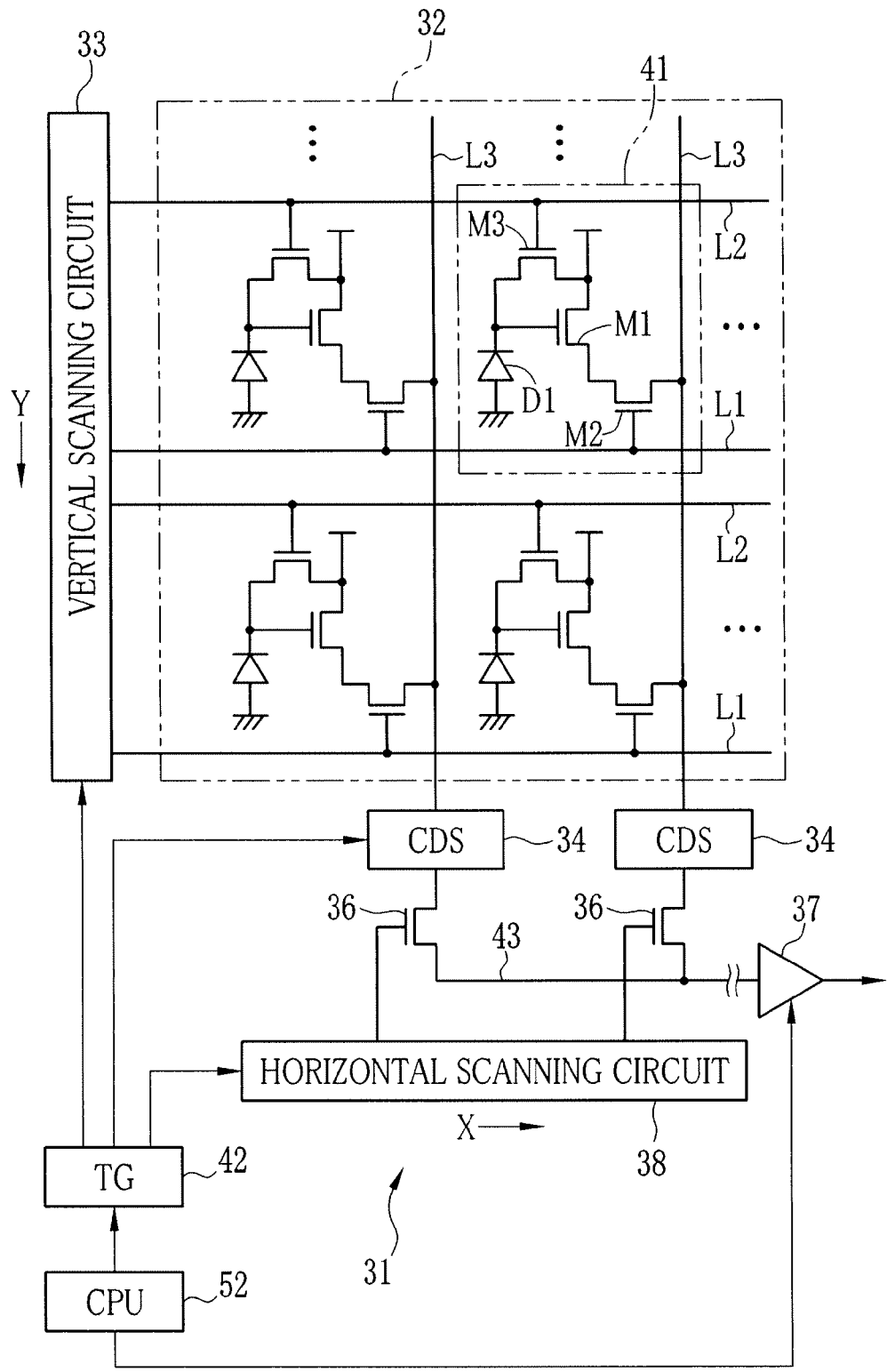
FIG. 3 is a circuit diagram of a CMOS image sensor.

As shown in FIG. 3, the CMOS sensor 31 is generally composed of an image capturing field 32, a vertical scanning circuit 33, correlated double sampling (CDS) circuits 34, column selection transistors 36, an output circuit 37 and a horizontal scanning circuit 38. Across the image capturing field 32, a plurality of row selection lines L1 and row reset lines L2 extend in a horizontal direction (X direction) from the vertical scanning circuit 33, and a plurality of column signal lines L3 extend in a vertical direction (Y direction) from the horizontal scanning circuit 38.

The image capturing field 32 includes a plurality of pixels 41 in a matrix arrangement. The image of an internal body part is focused onto the image capturing field 32 through the image capturing window 54 and an objective lens 51. The pixel 41 is composed of a photodiode D1, an amplifying transistor M1, a pixel selection transistor M2 and a reset transistor M3. The photodiode D1 generates and accumulates a signal charge proportional to the intensity of incident light. The accumulated signal charge is then amplified as an image signal (voltage signal) by the amplifying transistor M1. This image signal is transmitted through the pixel selection transistor M2 to the corresponding column signal line L3 at a predetermined timing. The signal charge in the photodiode D1 is then released or removed through the reset transistor M3 at a predetermined timing.

Each of the row selection lines L1 is connected to gates of the pixel selection transistors M2 on the same row, and each of the row reset lines L2 is connected to gates of the reset transistors M3 on the same row. Each of the column signal lines L3 is connected to sources of the pixel selection transistors M2 on the same column, and also to the corresponding column selection transistor 36 by way of the CDS circuit 34.

The vertical scanning circuit 33 generates a vertical scanning signal upon receiving a timing signal from the TG 42. Every time the vertical scanning signal is generated, the row selection lines L1 are selected sequentially from a first horizontal line (for example, the uppermost line in the image capturing field 32), and the image signals are read out from the pixels 41 on the selected horizontal line. At the same time, the vertical scanning circuit 33 selects the row reset lines L2 one by one from the first row, and releases the signal charges of the pixels 41 immediately after the image signal readout. When it reaches the row selection line L1 and the row reset line L2 of the last row (for example, the lowermost row in the image capturing field 32), and still receives the vertical scanning signal, then the vertical scanning circuit 33 selects the first horizontal line to repeat the same procedure.

The CDS circuit 34 holds the image signals of one selected horizontal line and removes the noise from them upon receiving a timing signal from the TG 42.

The horizontal scanning circuit 38 generates a horizontal scanning signal upon receiving a timing signal from the TG 42, and turns on and off the column selection transistors 36.

Each of the column selection transistors 36 bridges the corresponding CDS circuit 34 and an output bus line 43 connected to the output circuit 37. Upon receiving the horizontal scanning signal, the column selection transistor 36 transfers the image signal of the pixel 41 from the CDS circuit 34 to the output bus line 43. The output circuit 37 amplifies the image signals coming serially from the output bus line 43, and transmits the amplified image signals to the A/D converter 45. The amplification factor of the output circuit 37 may be changeable by entering an amplification adjustment signal.

Figure 2:
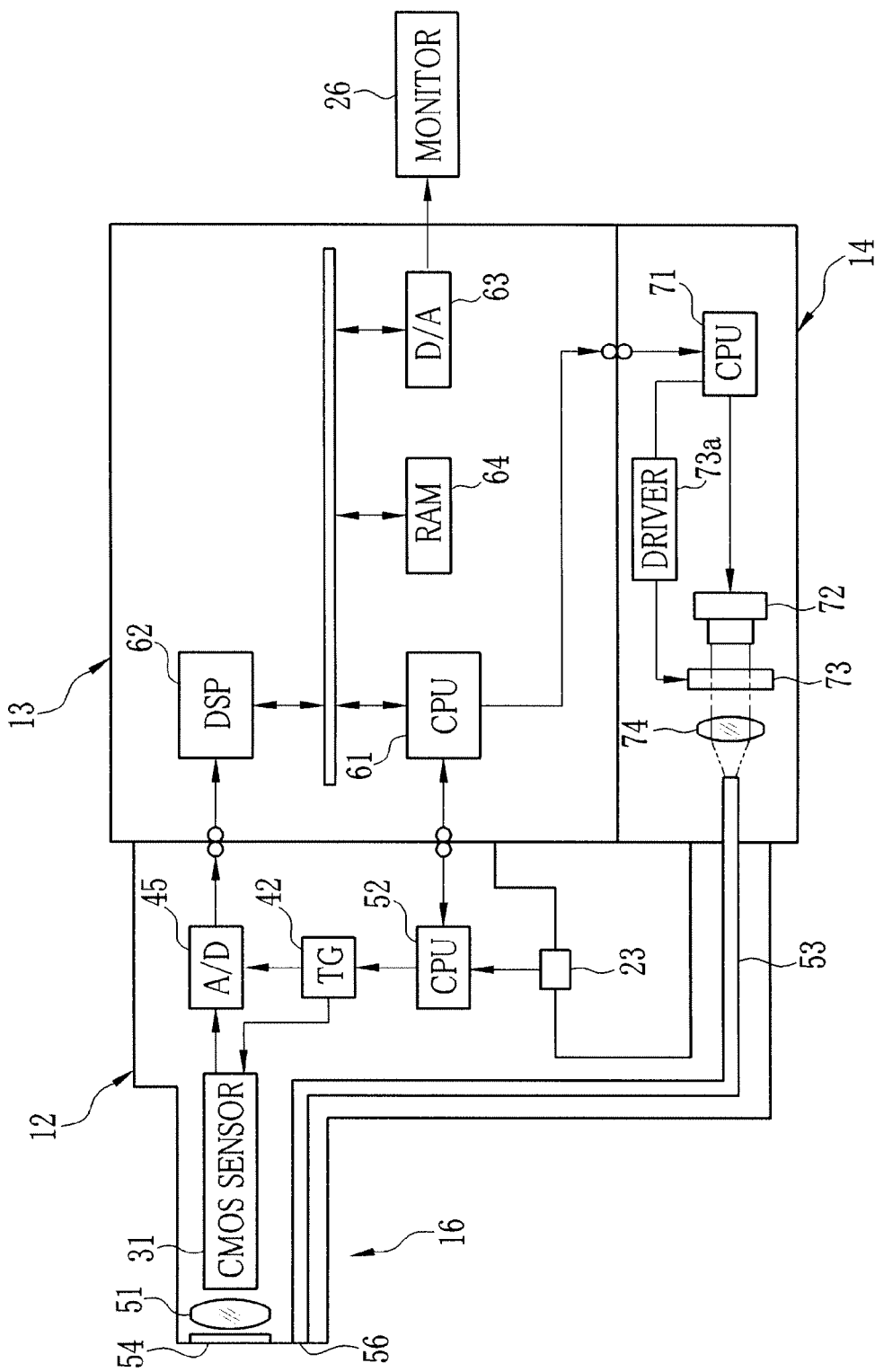
FIG. 2 is a block diagram of the electronic endoscope system.

As shown in FIG. 2, the distal portion 16a of the insertion section 16 holds a CMOS image sensor (hereinafter, CMOS sensor) 31. On the front face of the distal portion 16a, there are provided an illumination window 56 for emitting illumination light transmitted through a light guide 53, an image capturing window 54 for collecting the reflected light in the patient's body and transmitting it to the CMOS sensor 31, a forceps outlet port for projecting a medical instrument into the body cavity and an air/water nozzle for discharging air or rinse water (both not shown).

Figure 4:
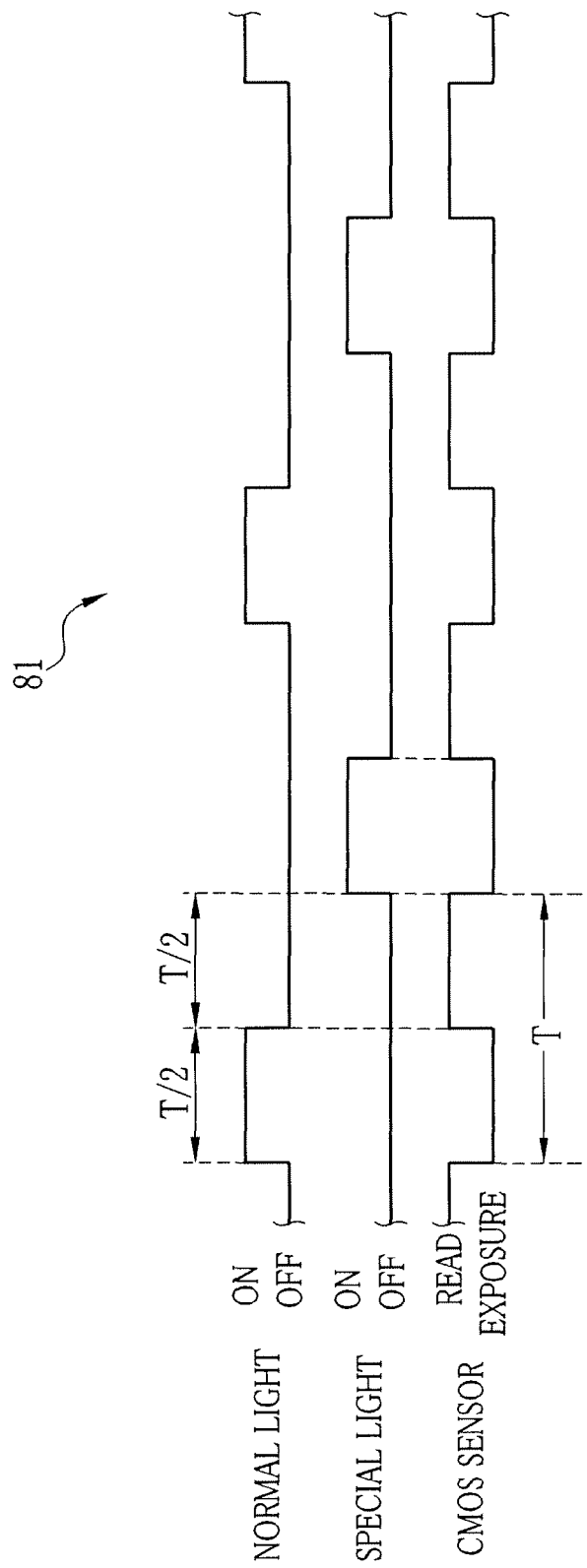
FIG. 4 is a timing diagram illustrating the relation ship between the switching of illumination light and the operation of the image sensor in a first imaging mode.

As shown in FIG. 4, in the first imaging mode 81, the light source 72 is turned on and off repeatedly based on a period T corresponding to one frame period. This period T is the time taken to read out the image signals from all the pixels 41 of the CMOS sensor 31, and is 1/30 second in this embodiment. More specifically, the light source 72 is turned on (i.e., the pixels are exposed) in every first half period T/2 (1/60 second), and it is turned off in every second half period T/2. The normal light and the special light are switched alternately every time the light source 72 is turned on.

Additionally, in the first imaging mode 81, the image signals are read out while the light source 72 is turned off. At this point, the image signals are read out from the pixels on every other horizontal line, not from all the pixels 41 in the image capturing field 32. The number of pixels is thereby reduced by half, when compared to the standard imaging mode. Although the image quality is somewhat sacrificed, the time to read out the image signals can be cut in half. The normal light images and the special light images are thus obtained without lowering the frame rate.

In the first imaging mode 81, the normal light and the special light are switched in each period T as is described above, and the normal light images and the special light images are alternately produced.

The CMOS sensor 31 in the first imaging mode 81 is controlled as follows. Firstly, all the pixels 41 in the image capturing field 32 are exposed for the same time (T/2) in the first half period T/2. After the exposure for the T/2 period, the processing device 13 directs the TG 42 to generate a particular timing signal for the first imaging mode 81.

Receiving this timing signal, the vertical scanning circuit 33 selects every other row selection line L1, from the top to the bottom, in the second half period T/2. The image signals are thus read out from every other horizontal line. Upon completion of the signal read out from one horizontal line, the vertical scanning circuit 33 selects two successive row reset lines for this already-read horizontal line and the next skipped horizontal line. The signal charges are then released from the pixels 41 on the already-read horizontal line and the skipped horizontal line. These reset pixels 41 are now ready for the next exposure.

In the second imaging mode 82, the image signals are read out in the same length of time as the standard imaging mode, so as to offer the same image quality as the standard imaging mode.

Figure 5:
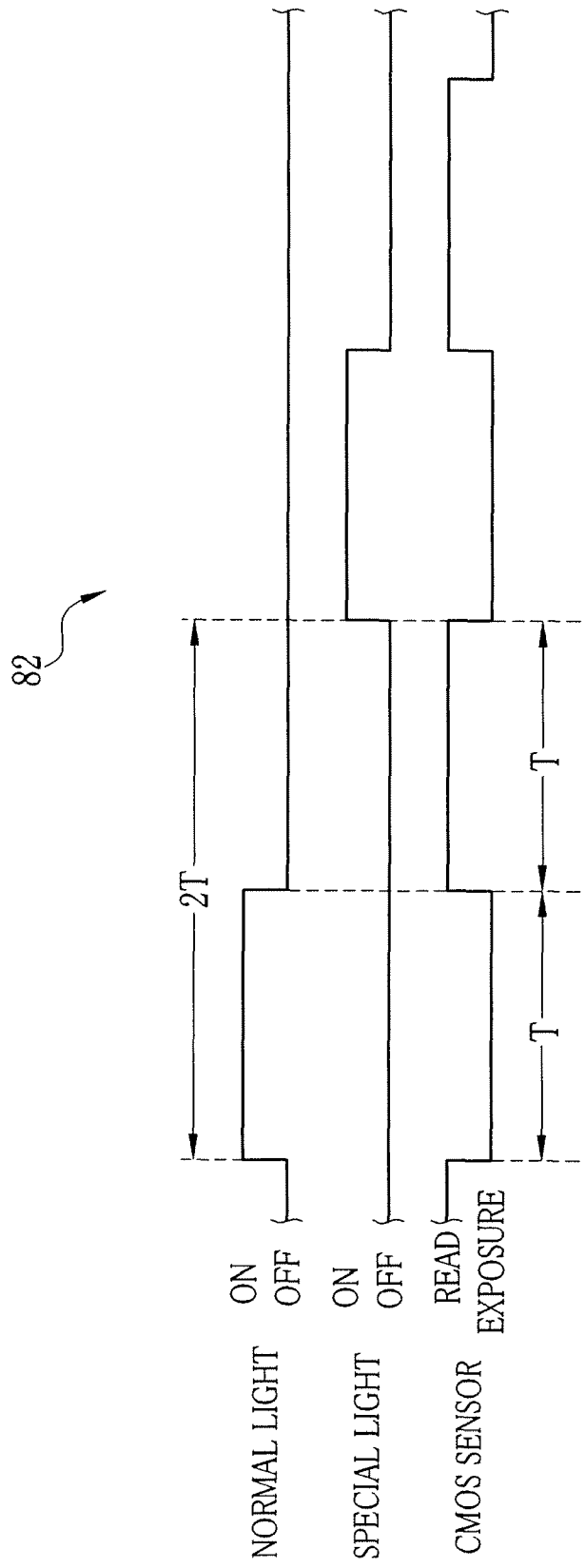
FIG. 5 is a timing diagram illustrating the relation ship between the switching of the illumination light and the operation of the image sensor in a second imaging mode.

As shown in FIG. 5, in the second imaging mode 82, the light source 72 is turned on and off repeatedly based on a period 2T. More specifically, the light source 72 is turned on in every preceding period T, and it is turned off in every succeeding period T. The normal light and the special light are switched alternately every time the light source 72 is turned on. Additionally, the image signals are read out from all the pixels 41 in the image capturing field 32 while the light source 72 is turned off. The resultant endoscopic images come with the same image quality as those in the standard imaging mode. While it takes the period 2T to produce a single image, the resultant endoscopic image shows the region of interest at high resolution, suitable for detailed observation.

The CMOS sensor 31 in the second imaging mode 82 is controlled as follows. Firstly, all the pixels 41 in the image capturing field 32 are exposed during the first T period. After the exposure for the T period, the processing device 13 directs the TG 42 to generate a particular timing signal for the second imaging mode 82.

Receiving this timing signal, the vertical scanning circuit 33 selects all the row selection lines L1, sequentially from the top to the bottom, in the second T period. Unlike the first imaging mode 81, the image signals are read out from all the pixels 41. Upon completion of the signal read out from one horizontal line, the vertical scanning circuit 33 selects the row reset line L2 for this already-read horizontal line. The signal charges are then released from the already-read horizontal line.

Figure 6A:
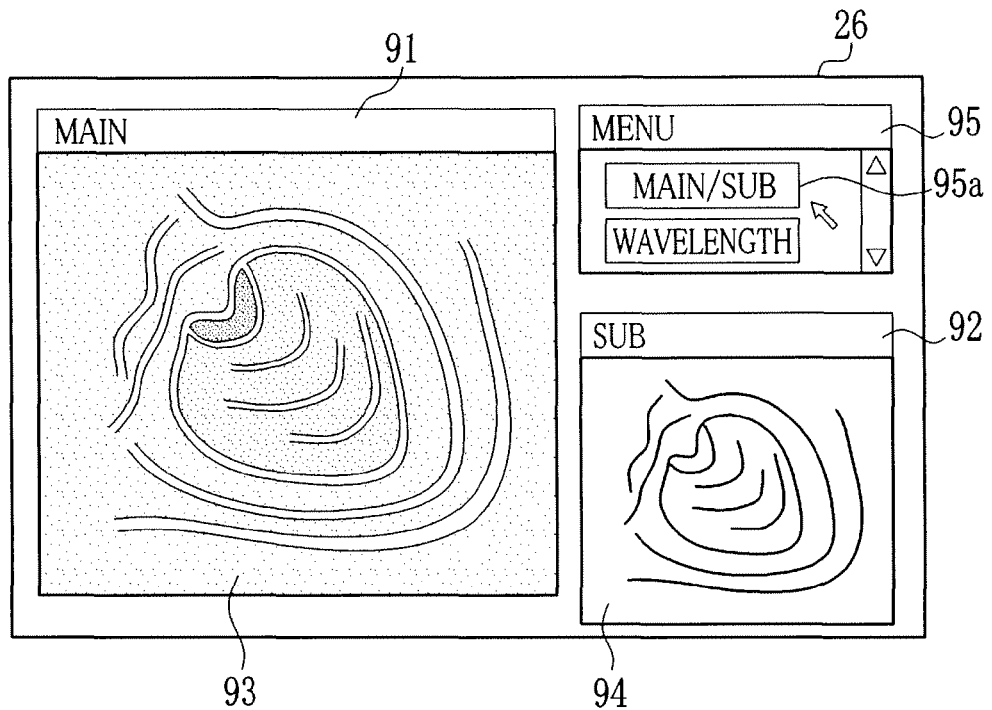
FIG. 6A and FIG. 6B are explanatory views of a monitor screen.
Figure 6B:
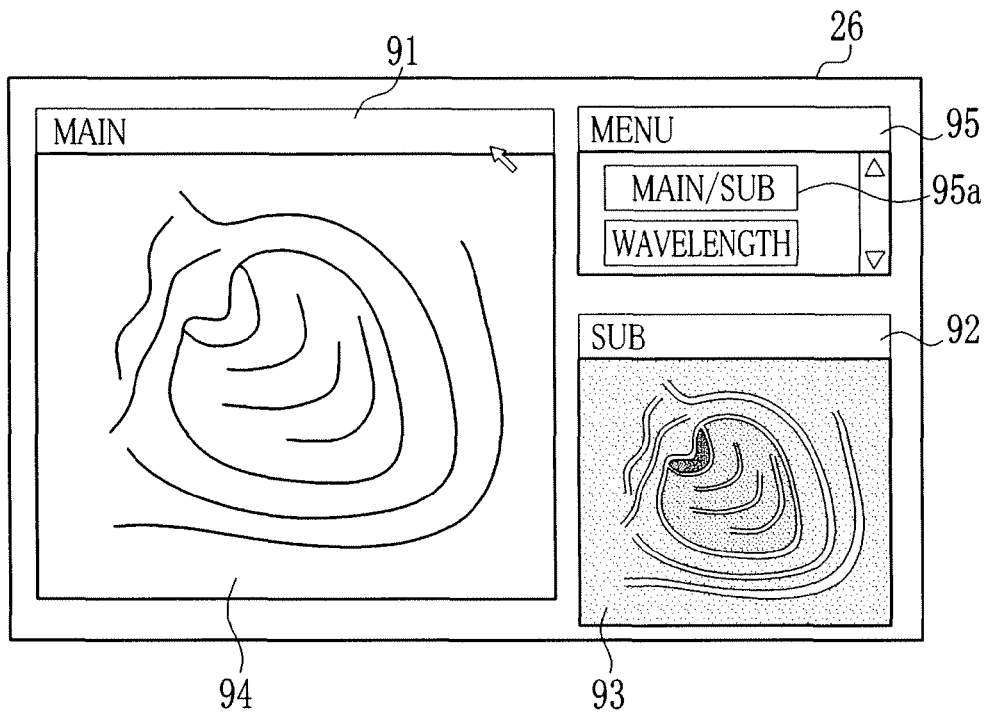

As shown in FIG. 6A, when the special imaging mode is selected, the monitor 26 provides a display screen having a main window 91 and a sub window 92. In this embodiment, the main window 91 displays a normal light image 93 and the sub window 92 displays a special light image 94. To enlarge the special light image 94, a main/sub button 95a in a menu window 95 can be clicked, and the special light image 94 is now displayed in the main window 91 as shown in FIG. 6B. Clicking on the main/sub button 95a again leads to return the normal light image 93 back in the main window 91 as shown in FIG. 6A.

Since the first imaging mode 81 uses the interlace scanning method, the image signals are read out in a short time. It is therefore possible to display the endoscopic image quickly. Accordingly, the first imaging mode 81 may be selected at the time while the insertion section 16 is inserted into a patient's body and advanced to the region of interest. In the second imaging mode 82, by contrast, the image signals are read out from all the pixels 41. Although the readout time is longer than in the first imaging mode, the second imaging mode 82 can produce as high resolution endoscopic images as the standard imaging mode produces. Because of this feature, the second imaging mode 82 may be selected after the insertion section 16 reaches the region of interest. During treatment using a medical instrument projected from the tip of the endoscope 12, however, the first mode may possibly be selected to quickly display a series of endoscopic images.

The normal light and the special light can be selected from any conventional illumination light, insofar as they have different wavebands.

By way of example, the special light may be infrared light for emphasizing the blood vessels, or visible light having one or more color spectrums for emphasizing the autofluorescence of normal and diseased tissues. These kinds of special light are preferably selectable in the electronic endoscope system 11. More preferably, the waveband of the special light is changeable during medical examination.

Although the image signals are read out from every other row in the first imaging mode 81 by selecting every other horizontal line, the image signals may be read out from every other column by changing the timing signal for the horizontal scanning circuit 38 to turn on every other column selection transistor 36. Alternatively, the timing signals for the vertical scanning circuit 33 and the horizontal scanning circuit 38 may be both changed to select the pixels 41 in a checkered pattern for signal readout.

In the first imaging mode 81, instead of resetting each of the horizontal lines immediately after the signal readout, it may be possible to firstly read out all the horizontal lines, and then reset them sequentially (or collectively) after an endoscopic image is produced. Alternatively, the selected horizontal lines may be reset immediately after the signal readout, and the skipped horizontal lines may be reset after an endoscopic image is produced.

Depending on the wavelength of the illumination light, the exposure time and the signal readout time in the first imaging mode 81 may be changed within the period T. When a long exposure time is desired, the exposure time may be extended to 2T/3 period, and the signal readout time may be reduced to T/3 period. In this case, the image signals are read out from one third of the pixels 41 so as to finish the signal readout in the T/3 period. On the contrary, when a short exposure time is desired, the exposure time may be reduced in some measure, and the signal readout time may be extended by that amount. In this case, the image signals are read out from as many pixels 41, more than half of the pixels 41, as possible in the signal readout time. This time adjustment allows for producing high resolution endoscopic images.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope system comprising:
   a complementary metal-oxide semiconductor (CMOS) image sensor having a plurality of pixels in a two dimensional array, said CMOS image sensor capturing an image of a region of interest under an illumination light and generating image signals;
   a light source device for repeatedly turning on and off a light source to emit said illumination light, said light source device switching a wavelength of said illumination light between at least two different wavebands every time said light source is turned on;
   a signal reader for reading out said image signals from all or a part of said pixels while said light source is turned off; and
   a signal processor for producing two kinds of endoscopic images based on said image signals read by said signal reader, wherein when a time taken to read out said image signals from all said pixels is defined as T, said light source device turns on said light source in every first T/2 period, and said signal reader reads out said image signals from half of said pixels in every second T/2 period.

2. The electronic endoscope system of claim 1, further comprising a monitor for displaying said two kinds of endoscopic images at once.

3. The electronic endoscope system of claim 1, wherein said signal reader uses an interlace scanning method to read out said image signals.

4. An electronic endoscope system comprising:
a complementary metal-oxide semiconductor (CMOS) image sensor having a plurality of pixels in a two dimensional array, said CMOS image sensor capturing an image of a region of interest under an illumination light and generating image signals;
a light source device for repeatedly turning on and off a light source to emit said illumination light, said light source device switching a wavelength of said illumination light between at least two different wavebands every time said light source is turned on;
a signal reader for reading out said image signals from all or a part of said pixels while said light source is turned off; and
a signal processor for producing two kinds of endoscopic images based on said image signals read by said signal reader,
wherein when a time taken to read out said image signals from all said pixels is defined as T, said light source device turns on said light source in every preceding T period, and said signal reader reads out said image signals from all said pixels in every succeeding T period.

5. The electronic endoscope system of claim 4, wherein said light source device turns on said light source during each first 2T/3 period, and said signal reader reads out said image signals from half of said pixels during each last T/3 period.

6. The electronic endoscope system of claim 1, wherein said light source device and said signal reader are operable on first and second imaging modes, and
in said first imaging mode, when the time taken to read out said image signals from all said pixels is defined as one frame period, said light source device turns on said light source in every first half of the frame period, and said signal reader reads out said image signals from half said pixels in every second half of the frame period, and
in said second imaging mode, when a frame rate of said first imaging mode is defined as N, a frame rate of said second imaging mode is N/2 and said image signals are read out from all said pixels.

7. The electronic endoscope system of claim 1, further comprising a resetting device for releasing signal charges from said pixels after the reading out of said imaging signals every time said light source is turned off.

8. The electronic endoscope system of claim 7, wherein said resetting device resets said pixels on a same horizontal line of the image at once.

9. The electronic endoscope system of claim 7, wherein said resetting device resets all said pixels at once.

10. The electronic endoscope system of claim 7, wherein said time T is 1/30 of a second.

11. The electronic endoscope system of claim 1, wherein said time T corresponds to one frame period.

12. The electronic endoscope system of claim 1, wherein the light source comprises a plurality of diodes.

13. The electronic endoscope system of claim 12, wherein each of the plurality of diodes are turned on and off separately.

* * * * *